United States Patent [19]

Bandurco et al.

[11] Patent Number: 4,656,267

[45] Date of Patent: * Apr. 7, 1987

[54] SUBSTITUTED 2(1H)-QUINAZOLINONE-1-ALKANOIC ACIDS AND ESTERS

[75] Inventors: Victor T. Bandurco, Bridgewater; Seymour D. Levine, North Brunswick, both of N.J.; Dennis M. Mulvey, New Hope; Alfonso J. Tobia, Doylestown, both of Pa.

[73] Assignee: Ortho Pharmaceutical Corporation, Raritan, N.J.

[*] Notice: The portion of the term of this patent subsequent to Nov. 26, 2002 has been disclaimed.

[21] Appl. No.: 627,138

[22] Filed: Jul. 2, 1984

Related U.S. Application Data

[63] Continuation-in-part of Ser. No. 537,233, Sep. 29, 1983, Pat. No. 4,555,571.

[51] Int. Cl.$^4$ .................. C07D 413/04; C07D 403/04; C07D 239/80
[52] U.S. Cl. .................................... 544/119; 544/116; 544/166; 544/286; 544/395
[58] Field of Search ............... 544/284, 285, 286, 116, 544/119

[56] References Cited

U.S. PATENT DOCUMENTS

| | | | |
|---|---|---|---|
| 4,001,238 | 1/1977 | Partyka et al. | 544/286 |
| 4,146,712 | 3/1979 | Yamamoto et al. | 544/286 |
| 4,490,374 | 12/1984 | Bandurco et al. | 544/286 |
| 4,555,570 | 11/1985 | Kanojia et al. | 544/286 |
| 4,555,571 | 11/1985 | Bandurco et al. | 544/116 |

FOREIGN PATENT DOCUMENTS 2127823A 4/1984 United Kingdom ................ 544/286

OTHER PUBLICATIONS

Lucas, *Organic Chemistry*, Sec. Ed., 1953, American Book Co., New York, pp. 211–215.
Morrison et al, *Organic Chemistry*, Sec. Ed., 1966, Allyn and Bacon, Inc., Boston, pp. 969–971.

*Primary Examiner*—Glennon H. Hollrah
*Assistant Examiner*—James H. Turnipseed
*Attorney, Agent, or Firm*—Benjamin F. Lambert

[57] ABSTRACT

The synthesis of substituted 2(1H)-quinazolinone-1-alkanoic acids and their esters is described. The novel quinazolinones are renal vasodilators and as such reduce vascular resistance to renal blood flow. The quinazolinones are useful as cardiovascular agents.

1 Claim, No Drawings

SUBSTITUTED 2(1H)-QUINAZOLINONE-1-ALKANOIC ACIDS AND ESTERS

This is a continuation-in-part of application Ser. No. 537,233, filed Sept. 29, 1983 and now U.S. Pat. No. 4,555,571.

The present invention relates to substituted quinazolinones having functionality at $N_1$. The substituted quinazolinones which are the subject of this invention have the following structural formula:

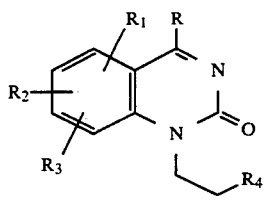

wherein
R is hydrogen or lower alkyl having 1-3 carbon atoms;
$R_1$ is hydrogen, lower alkyl having 1-3 carbon atoms, lower alkoxy having 1-4 carbon atoms, morpholino, methylpiperazino, hydroxy, alkoxycarbonyloxy wherein the alkoxy group has 1-4 carbon atoms, alkylamino wherein the alkyl group has 1-4 carbon atoms, halo, ureido, alkylthio wherein the alkyl group has 1-4 carbon atoms, alkyl sulfinyl wherein the alkyl group has 1-4 carbon atoms and alkanoyloxy having 2-5 carbon atoms;
$R_2$ is hydrogen, lower alkoxy having 1-4 carbon atoms, alkoxycarbonyloxy wherein the alkoxy group has 1-4 carbon atoms, hydroxy, alkylamino wherein the alkyl group has 1-4 carbon atoms, and alkanoyloxy having 2-5 carbon atoms;
$R_3$ is hydrogen, hydroxy and lower alkoxy having 1-4 carbon atoms;
$R_4$ is carboxy and carboalkoxy wherein the alkoxy group has 1-3 carbon atoms; and the pharmaceutically acceptable acid addition salts thereof such as, for example, the hydrochlorides, the hydrobromides and the hydroiodides.
provided that $R_1$, $R_2$ and $R_3$ are not simultaneously hydrogen.

Substituted 2(1H)-quinazolinones have been reported in the literature [Budesinsky et al., *Coll. Czech. Chem. Commun.*, 37, 2779 (1972). Belgian Pat. No. 765947 (11)]. However, none of the reported substituted quinazolinones are substituted with an acid residue at the $N_1$ position.

The novel substituted 2(1H)-quinazolinones of the present invention are renal vasodilators. As such they reduce vascular resistance to renal blood flow and are therefore useful as cardiovascular agents.

The substituted quinazolinones can be synthesized according to the following schematic diagram:

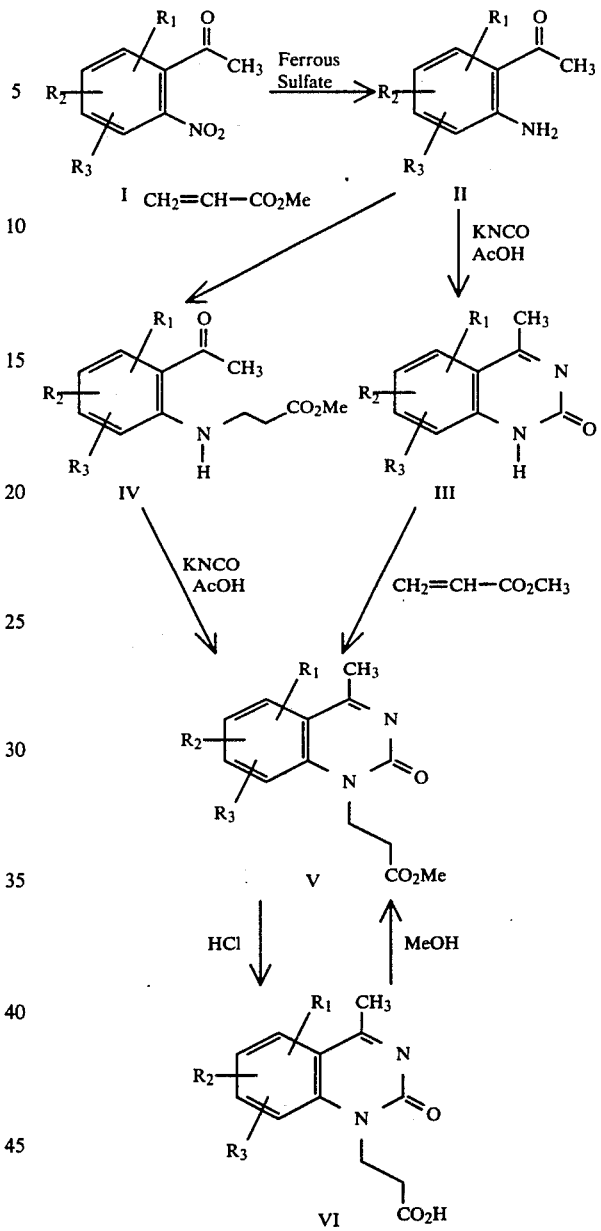

wherein $R_1$, $R_2$ and $R_3$ are as defined above.

As can be seen from the diagram, the substituted quinazolinones (V & VI) can be prepared by first reacting an appropriately substituted quinazolinone (III) with an olefinic ester such as methyl acrylate to form the corresponding substituted 2(1H)-quinazolinone-1-alkanoic acid ester. The reaction is preferably carried out at the reflux temperature of the solvent employed, although temperatures between $-10°$ C. and $100°$ C. may be employed depending upon the particular solvent used in the reaction. Suitable solvents include chloroform and methanol. The reaction is generally carried out in the presence of a catalyst such as, for example, sodium carbonate, triethylamine, alkali metal alkoxides and quaternary ammonium hydroxides such as tetramethylammonium hydroxide. Alternatively, the substituted quinazolinones can be prepared from an appropriately substituted N-(2-acyl)-β-alanine (IV) by reaction with an alkali metal cyanate such as, for example, potassium cyanate in a suitable solvent such as acetic acid. The reaction is generally carried out at a temperature between 0° C. and about 15° C. The N-(2-acyl)-β-alanine is prepared from an appropriately substituted 2o-acyl analine (II). The quinazolinone is obtained in the form of the ester. The free acid is then obtained by acid hydrolysis by techniques known to those skilled in the art. Alternatively the free acid quinazolinone (VI) can be prepared by reacting an appropriately substituted quinazolinone (III) or an appropriately substituted ketone (II) with an olefinic acid such as acrylic acid.

Those compounds wherein $R_3$ is hydrogen and $R_1$ and $R_2$ are both alkanoyloxy or alkoxycarbonyloxy can also be prepared by reacting a dihydroxy quinazolinone-1-alkanoic acid with an acid anhydride such as acetic anhydride, in the case where $R_2$ and $R_3$ are alkanoyloxy or with an alkyl chloroformate such as ethyl chloroformate, in the case where $R_2$ and $R_3$ are alkoxylcarbonyloxy. The hydroxyquinazolinones are prepared from the alkoxyquinazolinones by dealkylation with a suitable acid such as hydrobromic or hydrochloric acid.

The $N_1$ substituted quinazolinones (V and VI) can also be used as the starting materials for the preparation of other $N_1$ substituted quinazolinones falling within the generic structure.

The starting materials (quinazolinones) used to prepare the substituted 2(1H) quinazolinone alkanoic esters and acids (V and VI) can be prepared according to the methods described in copending U.S. application Ser. No. 430,552 filed Sept. 30, 1982, now U.S. Pat. No. 4,490,374 all of which methods are hereby incorporated by reference. Alternatively, the quinazolinones (III) can be prepared by first reducing an appropriately substituted acyl nitrobenzene to the corresponding amine and cyclyzing the amine to form the quinazolinone with a cyclizing agent such as potassium cyanate.

Pharmaceutical compositions containing a compound of the present invention as the active ingredient in intimate admixture with a pharmaceutical carrier can be prepared according to conventional pharmaceutical compounding techniques. The carrier may take a wide variety of forms depending on the form of preparation desired for administration, e.g., intravenous, oral or parenteral. In preparing the compositions in oral dosage form, any of the usual pharmaceutical media may be employed, such as, for example, water, glycols, oils, alcohols, flavoring agents, preservatives, coloring agents and the like in the case of oral liquid preparations such as, for example, suspensions, elixirs and solutions; or carriers such as starches, sugars, diluents, granulating agents, lubricants, binders, disintegrating agents and the like in the case of oral solid preparations such as, for example, powders, capsules and tablets. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, to aid solubility or for preservative purposes, may be included. Injectable suspensions may also be prepared, in which case appropriate liquid carriers, suspending agents and the like may be employed. The pharmaceutical compositions will generally contain, per dosage unit, e.g., tablet, capsule, powder, injection, teaspoonful and the like, from about 15 to about 300 mg/kg and preferably from about 30 to about 200 mg/kg of the active ingredient.

The following examples describe the invention in greater particularity and are intended to be a way of illustrating but not limiting the invention.

EXAMPLE 1

4-Methyl-6-(4-morpholino)-2(1H)-quinazolinone-1-propionic acid

A solution of methyl 6-(4-morpholino)-4-methyl-2(1H)-quinazolinone-1-propionate (1.10 g, 3.32 mmoles) in 50 ml of 2N hydrochloric acid is stirred at room temperature overnight. The solution is then washed with methylene chloride (2×50 ml) and brought to pH 4 with 1N NaOH solution. This solution is continuously extracted with ethyl acetate for 48 hours using fresh solvent every 24 hours. The ethyl acetate layers are combined and evaporated to dryness and the residue is recrystallized from methanol to give the desired product as the ¼ hydrate (0.45 g, 43%) mp 261° C.

4-Ethyl-6-(4-morpholino)-2(1H)-quinazolinone-1-propionic acid

Following the procedure of Example 1, but substituting methyl 6-(4-morpholino)-4-ethyl-2(1H)-quinazolinone-1-propionate for methyl 6-(4-morpholino)-4-methyl-2(1H)-quinazolinone-1-propionate affords the title compound.

EXAMPLE 2

Methyl 4-methyl-6-(4-morpholino)-2(1H)-quinazolinone-1-propionate

A solution of 4-methyl-6-(4-morpholino)-2(1H)-quinazolinone (0.44 g, 1.8 mmoles) in 10 ml of 4:1 $CHCl_3$:$CH_3OH$ is treated with methyl acrylate (1.62 ml, 18 mmoles) and Triton B (0.5 ml). The mixture is heated at reflux for 18 hours and the solvents are removed at reduced pressure. The residue is taken up in 50 ml of water and extracted with methylene chloride. The organic layers are dried over $MgSO_4$ and evaporated. The residue is chromatographed on a silica gel column and eluted with methylene chloride-ethyl acetate (1:1). Fractions containing the product are combined and recrystallized from acetone (0.15 g, 25%) mp 138°–141° C., M+331.

4-Methyl-6-(4-morpholino)-2(1H)-quinazolinone is prepared by the method of Example 18 using 2-amino-5-(4-morpholino)acetophenone. The yield of 4-methyl-6-(4-morpholino)-2(1H)-quinazolinone is 48%, mp 233° (d).

2-Amino-5-(4-morpholino)acetophenone is prepared by dissolving 5-(4-morpholino)-2-nitro-acetophenone (18.5 g, 74 mmoles) in boiling ethanol (250 ml) and adding it with stirring to a boiling solution of ferrous sulfate heptahydrate (144 g) in water (750 ml). Concentrated ammonium hydroxide solution (175 ml) is added in 10 ml portions over ½ hour and the mixture is filtered through Celite. The filtrate is evaporated to remove ethanol and the aqueous solution is extracted with ethyl acetate. The organic layer is dried over $MgSO_4$, filtered and evaporated to dryness. The residue is recrystallized from ether, then from methanol-hexane to give 2-amino-5-(4-morpholino)acetophenone, mp 103°–106° C.

5-(4-Morpholino)-2-nitro-acetophenone is prepared by heating 5-chloro-2-nitro-acetophenone (16.93 g, 85.1 mmoles) to 110° C. in 75 ml of DMF containing 227 g (261 mmoles) of morpholine. After 4 hours the solution is cooled to room temperature and poured into 500 ml of ice water. The resultant precipitate is collected by suction filtration and washed with water giving 5-(4-morpholino)-2-nitro-acetophenone, mp 139°–141° C.

Methyl 4-ethyl-6-(4-morpholino)-2(1H)-quinazolinone-1-propionate

Following the procedure of Example 2, but substituting 4-ethyl-6-(4-morpholino)-2(1H)-quinazolinone for 4-methyl-6-(4-morpholino)-2(1H)-quinazolinone affords the title compound. 4-Ethyl-6-(4-morpholino)-2(1H)-quinazolinone is synthesized from 5-chloro-2-nitro-propiophenone as above.

EXAMPLE 3

A. Methyl 4-methyl-6-(4-methylpiperazino)-2(1H)-quinazolinone-1-propionate

Prepared by the method of Example 2 substituting 4-methyl-6-(4-methylpiperazino)-2(1H)-quinazolinone for the morpholino compound, $M^+344$.

6-(4-Methylpiperazino)-4-methyl-2(1H)-quinazolinone is prepared from 2-amino-5-(4-methylpiperazino)acetophenone by the method of Example 18, $M^+258$, mp 263°–265° (d).

2-Amino-5-(4-methylpiperazino)acetophenone is prepared from 5-(4-methylpiperazino)-2-nitro-acetophenone by the method of Example 2, mp 90°–92° C., $M^+233$.

5-(4-Methylpiperazino)-2-nitro-acetophenone is prepared from N-methylpiperazine and 5-chloro-2-nitroacetophenone by the method of Example 2, mp 67°–69° C., $M^+263$.

B. 4-Methyl-6-(4-methylpiperazino)-2(1H)-quinazolinone-1-propionic acid

Prepared from the methyl ester described in Example 3A above by the method of Example 1, $M^+330$.

EXAMPLE 4

6,7-Diacetoxy-4-methyl-2(1H)-quinazolinone-1-propionic acid

To a slurry of 6,7-dihydroxy-4-methyl-2(1H)-quinazolinone-1-propionic acid (5.3 g, 20 mmoles) in 115 ml of pyridine is added 61.8 g (600 mmoles) of acetic anhydride. After 1 hour the reaction mixture is evaporated, the residue is treated with 100 ml of water and the pH is adjusted to 3.0 with 2N HCl. The slurry is stirred for 1 hour, extracted with $CH_2Cl_2$, dried and evaporated to a small volume. Ether is added and the product is collected by filtration, mp 140°–150° C., 1.7 g (24%).

EXAMPLE 5

6,7-Diisobutyloxy-4-methyl-2(1H)-quinazolinone-1-propionic acid

Using isobutyric anhydride in place of acetic anhydride in Example 4 gives the desired diisobutyloxy product, mp 126°–133° C., yield 24%.

EXAMPLE 6

6,7-Diethoxycarbonyloxy-4-methyl-2(1H)-quinazolinone-1-propionic acid

As in Example 4 using ethylchloroformate instead of acetic anhydride gives the 6,7-diethoxycarbonyloxy compound, mp 200°–205° C., $M^+408$.

EXAMPLE 7

6,7-Dipivaloyloxy-4-methyl-2(1H)-quinazolinone-1-propionic acid

To a slurry of 6,7-dihydroxy-4-methyl-2(1H)-quinazolinone-1-propionic acid (1 mmol) in 5 ml of trifluoroacetic acid is added 10 mmol of pivaloyl chloride. After stirring overnight, the reaction mixture is evaporated, the residue is treated with 100 ml of water and the pH is adjusted to 3.0 with 2N HCl. The slurry is stirred for 1 hour, extracted with $CH_2Cl_2$ and the methylene chloride is evaporated to dryness. The residue is extracted in a Soxhlet with ether. Evaporation of the ether gives the product (28%), mp 194°–200° C.

EXAMPLE 8

Methyl 4-methyl-5,6,7-trimethoxy-2(1H)-quinazolinone-1-propionate

4-Methyl-5,6,7-trimethoxy-2(1H)-quinazolinone is treated with methyl acrylate as in Example 2 to give the desired product as an oil, $M^+336$.

4-Methyl-5,6,7-trimethoxy-2(1H)-quinazolinone is prepared by adding 27.8 g (0.1 mmol) of 3,4,5-trimethoxyphenyl-N-acetyl urea to 280 g of polyphosphoric acid at 120° C. After 1 hour the reaction mixture is cooled, poured onto crushed ice and the pH is adjusted to 6.5 with $NH_4OH$. The product is collected and recrystallized from methanol to yield 9 g, mp 229°–230° C.

3,4,5-Trimethoxyphenyl-N-acetyl urea is prepared by heating a mixture of 3,4,5-trimethoxyphenylisocyanate (75.7 g, 0.36 mmol) and acetamide (21.4 g, 0.36 mmol) at 150° C. for 1 hour. The cooled mixture is triturated with acetone to give the desired product, mp 177°–179° C., (86 g).

EXAMPLE 9

Methyl 5,6-Dihydroxy-7-methoxy-4-methyl-2(1H)-quinazolinone-1-propionate

A methylene chloride solution of methyl 4-methyl-5,6,7-trimethoxy-2(1H)-quinazolinone-1-propionate (2.6 g) is treated with boron tribromide (25 g) at $-70°$ C. for 15 minutes and then room temperature for 5 hours. Methanol (35 ml) is slowly added, the reaction mixture is filtered, evaporated and the residue is triturated with ether (100 ml)/acetone (20 ml) for 2 days. The product is isolated as a hydrobromide, ¼ hydrate, (yield 1.27 g), mp > 300° C.

EXAMPLE 10

Methyl 6-dimethylamino-4-methyl-2(1H)-quinazolinone-1-propionate

Replacing the morpholino quinazolinone of Example 2 with 6-dimethylamino-4-methyl-2(1H)-quinazolinone gives methyl 6-dimethylamino-4-methyl-2(1H)-quinazolinone-1-propionate (64% yield). The compound is dissolved in tetrahydrofuran/ether and hydrogen bromide gas is bubbled in to give the desired product as a dihydrobromide ¾ hydrate, (mp 105°–107° C.).

6-Dimethylamino-4-methyl-2(1H)-quinazolinone is prepared by the treatment of 2-amino-5-dimethylaminoacetophenone with potassium cyanate as in Example 18, (mp 278°–281° C.).

2-Amino-5-dimethylaminoacetophenone is obtained by the iron reduction of 5-dimethyl-2-nitro-aminoacetophenone as in Example 12, (mp 68°–71° C.).

5-Dimethylamino-2-nitro-acetophenone is prepared from 5-chloro-2-nitro-acetophenone and dimethylamine according to the method of J. Beck, J. Org. Chem., 39, 1839 (1974), mp 148°–150° C.

Methyl 6-dimethylamino-2(1H)-quinazolinone-1-propionate

Replacing the morpholino quinazolinone of Example 2 with 6-dimethylamino-2(1H)-quinazolinone affords the title compound. 6-Dimethylamino-2(1H)-quinazolinone is synthesized from 2-nitro-5-chlorobenzaldehyde.

EXAMPLE 11

6-Dimethylamino-4-methyl-2(1H)-quinazolinone-1-propionic acid

Methyl 6-dimethylamino-4-methyl-2(1H)-quinazolinone-1-propionate is hydrolyzed as in Example 1 to give the title compound which is isolated as a hemihydrate in 69% yield, mp 231°–233° C.

6-Dimethylamino-2(1H)-quinazolinone-1-propionic acid

Methyl 6-dimethylamino-2(1H)-quinazolinone-1-propionate is hydrolyzed as in Example 1 to afford the title compound.

EXAMPLE 12

Methyl 7-dimethylamino-4-methyl-2(1H)-quinazolinone-1-propionate

Substitution of 6-(4-morpholino)-4-methyl-2(1H)-quinazolinone by 7-dimethylamino-4-methyl-2(1H)-quinazolinone as in Example 2 affords the title compound, mp 112°–115° C.

7-Dimethylamino-4-methyl-2(1H)-quinazolinone is prepared from 2-amino-4-dimethylaminoacetophenone and potassium cyanate as in Example 18, mp>300° C.

2-Amino-4-dimethylaminoacetophenone is prepared by adding iron powder (22 g) in portions to 2-nitro-6-dimethylaminoacetophenone (10.8 g) in acetic acid (71 ml) and water (71 ml). The suspension is heated at 95° C. for 3 hours, cooled and filtered. The resulting solid is triturated with chloroform; filtration followed by evaporation gives the diaminoacetophenone, (4.2 g, mp 104°–107° C.).

2-Nitro-4-dimethylaminoacetophenone is prepared from 4-chloro-2-nitroacetophenone and dimethylamine as in Example 10, (mp 155°–158° C.).

EXAMPLE 13

Methyl 6-dimethylamino-7-chloro-4-methyl-2(1H)-quinazolinone-1-propionate

Using 6-dimethylamino-7-chloro-4-methyl-2(1H)-quinazolinone instead of 6-dimethylamino-4-methyl-2(1H)-quinazolinone in Example 10 gives the title compound as the dihydrobromide in 77% yield, (mp: softens at 82° C., decomposes at 110° C.).

7-Chloro-6-dimethylamino-4-methyl-2(1H)-quinazolinone is obtained from the reaction of the corresponding 2-aminoacetophenone and potassium cyanate as in Example 18.

4-Chloro-5-dimethylamino-2-aminoacetophenone is prepared by the iron reduction of 4-chloro-5-dimethylamino-2-nitroacetophenone as in Example 12, (mp 72°–74° C.).

4-Chloro-5-dimethylamino-2-nitro-acetophenone is prepared by the reaction of 4,5-dichloro-2-nitroacetophenone with dimethylamine as in Example 10, (mp 129°–131° C.).

EXAMPLE 14

7-Chloro-6-dimethylamino-4-methyl-2(1H)-quinazolinone-1-propionic acid

Methyl 7-chloro-6-dimethylamino-4-methyl-2(1H)-quinazolinone-1-propionate is hydrolyzed by the procedure of Example 1 to give the free acid. The product (24% yield) is obtained as a ¾ hydrate, (mp 114°–116° C.).

EXAMPLE 15

Methyl 6,7-dimethoxy-4,5-dimethyl-2(1H)-quinazolinone-1-propionate

The use of 6,7-dimethoxy-4,5-dimethyl-2(1H)-quinazolinone in Example 2 in place of 6-(4-morpholino)-4-methyl-2(1H)-quinazolinone yields the title compound in 50% yield, (mp 110°–114° C.).

6,7-Dimethoxy-4,5-dimethyl-2(1H)-quinazolinone is prepared by the potassium cyanate method of Example 18 starting with 2-amino-4,5-dimethoxy-6-methylacetophenone, (mp 242°–245° C.).

2-Amino-4,5-dimethoxy-6-methyl-2-nitroacetophenone by iron reduction as in Example 12, (mp 78°–81° C.).

The 2-nitro derivative (mp 78°–81° C.) is obtained by nitration of 3,4-dimethoxy-2-methyl-acetophenone [R. Borchardt, P. Bhatia, J. Med. Chem. 25, 263 (1981)] as in Example 22.

Methyl 4-butyl-6,7-dimethoxy-5-methyl-2(1H)-quinazolinone-1-propionate

The use of 4-butyl-6,7-dimethoxy-5-methyl-2(1H)-quinazolinone in Example 2 in place of 6-(4-morpholino)-4-methyl-2(1H)-quinazolinone affords the title compound. 4-Butyl-6,7-dimethoxy-5-methyl-2(1H)-quinazolinone is synthesized from 3,4-dimethoxy-2-methylvalerophenone.

EXAMPLE 16

6,7-Dihydroxy-4,5-dimethyl-2(1H)-quinazolinone-1-propionic acid hydrobromide

Methyl 6,7-dimethoxy-4,5-dimethyl-2(1H)-quinazolinone-1-propionate (1.3 g, 4.06 mmol) is heated in 48% aqueous hydrobromic acid (15 ml) and glacial acetic acid (31 ml) at reflux for 65 hours. The reaction mixture is cooled and the product is removed by filtration. The crude solid is treated first with ether and then with hexane and dried to afford the product as a hydrobromide ¼ hydrate, (0.8 g, mp 291°–293° C.).

4-Butyl-6,7-dihydroxy-5-methyl-2(1H)-quinazolinone-1-propionic acid

The use of 4-butyl-6,7-dimethoxy-5-methyl-2(1H)-quinazolinone-1-propionate in place of methyl 6,7-dimethoxy-4,5-dimethyl-2(1H)-quinazolinone-1-propionate in Example 16 above affords the title compound.

EXAMPLE 17

Methyl 6,7-dihydroxy-4,5-dimethyl-2(1H)-quinazolinone-1-propionate

Esterification of 6,7-dihydroxy-4,5-dimethyl-2(1H)-quinazolinone-1-propionic acid with methanol using molecular sieves as a catalyst affords the desired product, (mp>300° C.).

EXAMPLE 18

5-Chloro-7,8-dimethoxy-4-methyl-2(1H)-quinazolinone-1-propionic acid

A solution of N-(2-acetyl-3-chloro-5,6-dimethoxyphenyl)-β-alanine (4.56 g, 11.9 mm) in acetic acid (115 ml) is stirred at room temperature for 15 minutes, cooled in an ice-H$_2$O bath and potassium cyanate (2.54 g, 31.3 mm) is added. The mixture is stirred at room temperature for 20 minutes and then heated at 60°–65° C. for 4 hours. After cooling to room temperature, the reaction mixture is concentrated to dryness to give a semi-solid which is washed with cold water and crystallized from isopropanol to afford the desired product, (0.3 g, 7.8%, mp 80°–85° C.).

5-Chloro-7,8-dihydroxy-4-methyl-2(1H)-quinazolinone-1-propionic acid hydrobromide (mp 194–196) is made by treating 5-chloro-7,8-dimethoxy-4-methyl-2(1H)-quinazolinone with hydrobromic acid.

N-(2-Acetyl-3-chloro-5,6-dimethoxyphenyl)-β-alanine is prepared from 2-amino-6-chloro-3,4-dimethoxyacetophenone and acrylic acid as in Example 2, (oil, M+301).

2-Amino-6-chloro-3,4-dimethoxy-acetophenone is prepared by the iron reduction of 6-chloro-3,4-dimethoxy-2-nitroacetophenone as in Example 10, (oil, M+229).

6-Chloro-3,4-dimethoxy-2-nitroacetophenone is prepared from 6-chloro-3,4-dimethoxy-2-nitrobenzoic acid [J. F. Blunt, A. Erasmuson, R. Ferrier & M. Munro, Aust. J. Chem., 32, 1045 (1979)] via the acid chloride and diethyl ethoxymagnesiummalonate by the method of A. Kövendi and M. Kircz, Berichte, 97, 1902 (1964), (mp 68°–70° C.).

EXAMPLE 19

8-Chloro-6,7-dimethoxy-4-methyl-2(1H)-quinazolinone-1-propionic acid

When N-(2-acetyl-6-chloro-4,5-dimethoxyphenyl)-β-alanine is used in Example 18 in place of N-(2-acetyl-3-chloro-5,6-dimethoxy phenyl)-β-alanine the title compound is obtained, (mp 92°–97° C.).

The β-alanine starting material is prepared in an identical manner as the β-alanine in Example 18 using 3-chloro-4,5-dimethoxy-2-nitroacetophenone.

EXAMPLE 20

Methyl 6-fluoro-4-methyl-2(1H)-quinazolinone-1-propionate

6-Fluoro-4-methyl-2(1H)-quinazolinone is treated with methyl acrylate as in Example 2 to yield the title compound as an oil, M+264.

6-Fluoro-4-methyl-2(1H)-quinazolinone is prepared by treatment of 2-amino-5-fluoroacetophenone with potassium cyanate as in Example 18 and is isolated as the ¼ hydrate, (mp 294°–296° C.).

2-Amino-5-fluoroacetophenone, (mp 63°–64.5° C.), is prepared from 2-aminoacetophenone by the method of D. Mulvey, et al., Tet. Letters, 16, 2319 (1978).

EXAMPLE 21

6-Fluoro-4-methyl-2(1H)-quinazolinone-1-propionic acid hydrochloride

Hydrolysis of methyl 6-fluoro-4-methyl-2(1H)-quinazolinone-1-propionate as in Example 1 yields the title compound which is isolated as the hydrochloride hemihydrate, (mp dec>235°), M+250.

EXAMPLE 22

Methyl-7-chloro-4-methyl-6-methylthio-2(1H)-quinazolinone-1-propionate

7-Chloro-4-methyl-6-methylthio-2(1H)-quinazolinone is treated with methyl acrylate as in Example 2 to give the title compound.

2-Amino-4-chloro-5-methylthioacetophenone is converted to 7-chloro-6-methylthio-4-methyl-2(1H)-quinazolinone hemihydrate with potassium cyanate as in Example 18, [mp 270°–274° (dec)].

2-Amino-4-chloro-5-methylthioacetophenone is prepared by adding to a solution of 4-chloro-5-methylthio-2-nitroacetophenone (10 g) in 50% aqueous ethanol (200 ml) 100 g of FeSO$_4$.7H$_2$O in 300 ml of hot water at 90° C. To the resulting solution is added dropwise 200 ml of concentrated NH$_4$OH. After 2 hours at reflux, the mixture is filtered, the filter cake and the aqueous filtrate are each extracted with methylene chloride. The extracts are combined and the solvent is removed to give the desired 2-amino-4-chloro-5-methylthioacetophenone, (mp 119°–121° C.).

4-Chloro-5-methylthio-2-nitroacetophenone is prepared by stirring a mixture of 1 equivalent of sodium hydride in methanol, 2 equivalents of methyl mercaptan in methanol and 1 equivalent of 2-nitro-4,5-dichloroacetophenone at 20° C. for 3 hours. The 4-chloro-5-methylthio-2-nitroacetophenone is collected by filtration, (mp 106°–108° C.).

2-Nitro-4,5-dichloroacetophenone is prepared by treating 10.0 g of 3,4-dichloroacetophenone in 80 ml of glacial acetic acid at 10° C. with 50 ml of 70% nitric acid. Stirring is continued for ½ hour after the addition and the product is isolated by filtration, (mp 98°–100° C.).

EXAMPLE 23

7-Chloro-4-methyl-6-methylthio-2(1H)-quinazolinone-1-propionic acid

Methyl 7-chloro-4-methyl-6-methylthio-2(1H)-quinazolinone-1-propionate is hydrolyzed by the method of Example 1 to give the title compound.

EXAMPLE 24

Methyl 4-methyl-6-methylthio-2(1H)-quinazolinone-1-propionate

The title compound is prepared by the method of Example 2 substituting 6-methylthio-4-methyl-2(1H)-quinazolinone for the morpholino compound. The product is isolated by preparative thin layer chromatography using ethermethylene chloride as the solvent system, M+190.

EXAMPLE 25

Methyl 7-chloro-4-methyl-6-ureido-2(1H)-quinazolinone-1-propionate

Treatment of 7-chloro-4-methyl-6-ureido-2(1H)-quinazolinone with methyl acrylate as in Example 2 affords the title ester.

The free acid, 7-chloro-4-methyl-6-ureido-2(1H)-quinazolinone-1-propionic acid is obtained from the ester by hydrolysis.

A solution containing 4-chloro-2,5-diaminoacetophenone (1.5 g, 8 mmoles) and sodium cyanate (1.16, 18 mmoles) in 30 ml acetic acid is treated as in Example 18 to give 7-chloro-4-methyl-6-ureido-2(1H)-quinazolinone, (mp>310° C.).

4-Chloro-2,5-diaminoacetophenone is prepared by iron reduction of 5-azido-4-chloro-2-nitroacetophenone as in Example 22, (mp 165°-167° C.).

5-Azido-4-chloro-2-nitroacetophenone is obtained from 4,5-dichloro-2-nitroacetophenone and sodium azide in dimethylformamide at room temperature for 2 hours.

EXAMPLE 26

Methyl 6-chloro-4-methyl-2(1H)-quinazolinone-1-propionate monohydrochloride

Substitution of 6-chloro-4-methyl-2(1H)-quinazolinone for 6-(4-morpholino)-4-methyl-2(1H)-quinazolinone in Example 2 gives the free base of the title compound which is converted to the hydrochloride salt in tetrahydrofuran with HCl(g). The hydrochloride salt was isolated by filtration and recrystallized from isopropanol, (mp 188°-190° C.).

6-Chloro-4-methyl-2(1H)-quinazolinone was synthesized as a tan solid, mp 286°-288° C., from 2-(N-carbethoxyamino)-4-chloroacetophenone by the reaction with ammonia and ammonium acetate.

2-(N-carbethoxyamino)-4-chloroacetophenone was synthesized from 2-amino-5-chloroacetophenone as a white solid, mp 63°-64° C., by reaction with ethylchloroformate and sodium hydroxide.

EXAMPLE 27

6-Chloro-4-methyl-2(1H)-quinazolinone-1-propionic acid

Substitution of methyl 6-chloro-4-methyl-2(1H)-quinazolinone-1-propionate monohydrochloride (6.0 g, 18.9 mm) for methyl 4-methyl-6-(4-morpholino)-2(1H)-quinazolinone-1-propionate in Example 1 affords the desired acid as the ¼ hydrate, 2.55 g (50%), mp 236°-238° C., M+266.

Using the appropriately substituted quinazolinone, 4-methyl-6-methylthio 2(1H)-quinazolinone-1-propionic acid is prepared according to the procedure of Example 22.

Using the appropriately substituted quinazolinones, methyl 7-chloro-4-methyl-6-methylsulfinyl-2(1H)-quinazolinone-1-propionate and 7-chloro-4-methyl-6-methylsulfinyl-2(1H)-quinazolinone-1-propionic acid are prepared by the procedure of Example 22.

Using the appropriately substituted quinazolinone, methyl 7-chloro-4-methyl-6-(4-methylpiperazino)-2(1H)-1-propionate and 7-chloro-4-methyl-6-(4-methylpiperazino)-2(1H)-1-propionic acid are prepared by the procedures of Example 3.

The renal vasodilator activity of the substituted quinazolinones is determined according to the following general procedure:

METHODS

Adult mongrel dogs are anesthetized and surgically prepared for electromagnetic measurement of renal artery blood flow. A carotid artery is annulated for measuring arterial blood pressure and drugs are administered intravenously. Heart rate (HR) is monitored by a cardiotachometer. Renal vascular resistance (RVR) is calculated as the ratio cf mean arterial blood pressure (MABP)/renal artery blood flow (RBF). Cumulative dose-response data are obtained by infusing the test drug at progressively increasing (usually three-fold) infusion rates, each dose being infused for five minutes. The maximum percent change from pre-drug control is quantitated for each parameter. Reductions in renal vascular resistance represent renal vasodilation. The activity of some representative compounds of this invention is listed below.

| | RENAL VASODILATOR ACTIVITY IN THE ANESTHETIZED DOG | | | | |
|---|---|---|---|---|---|
| | | TOTAL CUMULATIVE DOSE | PERCENT CHANGE FROM PRE-DRUG BASELINE | | |
| STRUCTURE | | mg/kg, i.v. | RBF | RVR | MABP | HR |
| 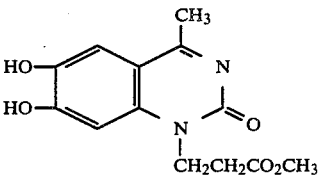 | | 15 | +65 | −44 | −10 | +10 |

-continued

RENAL VASODILATOR ACTIVITY IN THE ANESTHETIZED DOG

| STRUCTURE | TOTAL CUMULATIVE DOSE mg/kg, i.v. | PERCENT CHANGE FROM PRE-DRUG BASELINE | | | |
|---|---|---|---|---|---|
| | | RBF | RVR | MABP | HR |
| (structure: 3,4-dihydroxy-2-methyl phenyl with CH₃ C=N, fused ring N-C(=O)) | 30 | +23 | −41 | −26 | −9 |
| (structure: 4-(CH₃)₂N phenyl, CH₃ C=N, N-C(=O)) | 6.2 | +36 | −25 | +2 | 0 |
| (structure: 4-(CH₃)₂N phenyl, CH₃ C=N, N(CH₂CH₂CO₂CH₃)-C(=O)) | 8 | +10 | −12 | −4 | −9 |
| (structure: 4-(CH₃)₂N phenyl, CH₃ C=N, N(CH₂CH₂COOH)-C(=O)) | 30 | +9 | −6 | +2 | +5 |
| (structure: 4-(CH₃)₂N phenyl, CH₃ C=N, N(CH₂CH₂CO₂CH₃)-C(=O)) | 30 | +22 | −19 | −1 | +1 |
| (structure: 3,4,5-tri-CH₃O phenyl, CH₃ C=N, N(CH₂CH₂CO₂CH₃)-C(=O)) | 13.9 | +78 | −51 | −14 | −6 |

We claim:

1. A compound of the formula

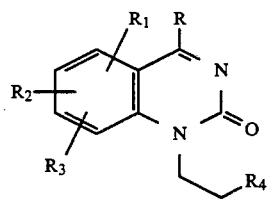

wherein R is hydrogen or lower alkyl; R₁ is hydrogen, lower alkyl, lower alkoxy, morpholine, methyl piperazino, hydroxy, alkoxyacrbonyloxy wherein the alkoxy group has 1-4 carbon atoms, alkylamino wherin the alkyl group has 1-4 carbon atoms, halo, ureido, alkylthio wherein the alkyl group has 1-4 carbon atoms, aklyl sulfinyl wherein the alkyl group has 1-4 carbon atoms and alkanoyloxy having 2-5 carbon atoms; R₂ is hydrogen, lower alkoxy, alkoxycarbonyloxy wherein the alkoxy group has 1-4 carbon atoms, hydroxy, alkylamino wherein the alkyl group has 1-4 carbon atoms and alkanoyloxy having 2-5 carbon atoms; R₃ is hydrogen, hydroxy and lower alkoxy; and R₄ is carboxy and carboalkoxy wherein the alkoxy group has 1-3 carbon atoms; and the pharmaceutically acceptable acid addition salts thereof, provided that R₁, R₂ and R₃ are not simultaneously hydrogen and when R₁ or R₂ or R₃ is hydrogen the remaining substituents are not hydroxy.

* * * * *

UNITED STATES PATENT AND TRADEMARK OFFICE
CERTIFICATE OF CORRECTION

PATENT NO. : 4,656,267
DATED : April 7, 1987
INVENTOR(S) : Victor T. Bandurco et al.

It is certified that error appears in the above—identified patent and that said Letters Patent is hereby corrected as shown below:

Column 13, Claim 1, line 63, "morpholine" should read --morpholino--.

Column 13, Claim 1, line 64, "alkoxyacrbonyloxy" should read --alkoxycarbonyloxy--.

Column 13, Claim 1, line 65, "wherin" should read --wherein--.

Column 14, Claim 1, line 53, "aklyl" should read --alkyl--.

Signed and Sealed this

Seventeenth Day of November, 1987

Attest:

DONALD J. QUIGG

*Attesting Officer*

*Commissioner of Patents and Trademarks*